United States Patent [19]
Morris

[11] Patent Number: 5,947,908
[45] Date of Patent: Sep. 7, 1999

[54] COLOR REACTIVITY DEVICE AND METHOD

[76] Inventor: Ritchi Morris, 648 Central Pk. Ave.-Ste 462, Scarsdale, N.Y. 10583

[21] Appl. No.: 08/801,552

[22] Filed: Feb. 18, 1997

Related U.S. Application Data

[63] Continuation-in-part of application No. 08/502,063, Jul. 14, 1995, abandoned.

[51] Int. Cl.[6] ........................................................ A61B 5/02
[52] U.S. Cl. .............................................. 600/484; 600/27
[58] Field of Search ................................. 600/21, 26–28, 600/382–385, 484; 601/15

[56] References Cited

U.S. PATENT DOCUMENTS

| | | |
|---|---|---|
| 4,289,121 | 9/1981 | Kupriyanovich . |
| 4,327,712 | 5/1982 | Frenkel et al. . |
| 4,388,918 | 6/1983 | Filley . |
| 4,665,926 | 5/1987 | Leuner et al. . |
| 4,777,937 | 10/1988 | Rush et al. ................................. 600/27 |
| 4,902,274 | 2/1990 | Gleeson, III . |
| 5,036,858 | 8/1991 | Carter et al. . |
| 5,064,410 | 11/1991 | Frenkel et al. . |
| 5,113,870 | 5/1992 | Rossenfeld . |
| 5,219,322 | 6/1993 | Weathers . |
| 5,243,517 | 9/1993 | Schmidt et al. . |
| 5,304,112 | 4/1994 | Mrklas et al. ........................ 600/27 X |
| 5,331,969 | 7/1994 | Silberstein . |

OTHER PUBLICATIONS

Thought Technology Ltd., *ProComp*.

*Primary Examiner*—Jeffrey R. Jastrzab
*Assistant Examiner*—Ryan Carter
*Attorney, Agent, or Firm*—Burd, Bartz & Gutenkauf

[57] ABSTRACT

An apparatus and method for deriving, with respect to a particular individual, those color hues which have particularly major impact upon the individual in terms of being most positive or most negative. The patient is subjected to a display of changing color hues and is fitted with a biofeedback assembly that measures involuntary body system responses as the individual views the display. These measurements are coordinated with the color display in order to identify each color shade's impact upon the individual. In one preferred embodiment, the color display is generated by a monochromatic light source in order to subject the patient to true or pure color.

11 Claims, 4 Drawing Sheets

COLOR REACTIVITY DEVICE AND METHOD

CROSS REFERENCE TO A RELATED APPLICATION

This application is a continuation-in-part of U.S. application Ser. No. 08/502,063 filed Jul. 14, 1995 now abandoned.

BACKGROUND OF THE INVENTION

In individuals, hues of color can act as a stimuli for either the creation of or relief of a stress condition. Each individual reacts to a given color hue differently. The individual may react negatively toward one shade and positively toward another. In part, this may be due to the fact that human experience, especially traumatic experiences, are all encoded in color somewhere in the brain. Particular color hues represent different experiences recorded from life in memory. Clinical experience has shown that patients continually reported that the majority of their internal material, especially trauma and post-trauma stress disorder material, was reported in association with color(s). Different hues of color have been shown to either elicit the various experiences, especially the physically and emotionally painful experiences, or that certain color hues seemed to dilute, eliminate or even block the painful experiences.

Certain bodily functions are susceptible to involuntary response upon the application of external stimuli. In particular, certain body function responses can be elicited from an individual by the application of external stimuli in the form of specific color hues that are influential upon the individual in either a positive or negative way. This propensity is unique to each individual, even amongst twins and triplets.

Isolating the individual's inborn, unconscious susceptibility to a particular hue, both in negative and positive senses, is a useful tool for the person to employ when performing in a wide variety of everyday experiences.

For example, research revealed a number of years ago that anxieties (defined as "inner tension") developed along a productivity/counter-productivity inverted-U curve ($\Omega$). The researchers showed that a certain amount of anxiety ("inner tension" and not what is commonly noted as "psychological anxiety"), is desirable and necessary to perform a task well, and that beyond a preferred range, performance actually declines. A hypothesis is that the ill effects of a person being inundated with their most negative shade can serve to heighten the amount of inner tension (anxiety) so as to create within that person an amount of anxiety beyond the preferred range with a resultant counter-productive state of performance. By employing their most positive, strengthening color hue, an individual can control the possible bombardment of negative, weakening effects of their most negative shade or shades. This end can be achieved by various means, such as tinting a protective face and/or eye shield in a sports setting, for example. In the world of academics, students and teachers can utilize the benefits of their most positive, strengthening hues for studying on a regular basis, in terms of retaining and reproducing material upon demand. The remedial processes of optimizing positive colors and reducing or eliminating the negative ones, can be applied to performances in other areas that cause stress and strain, such as (1) the world of work: for example, computer fatigue; continual and repetitive operation of machinery; performance in front of bright, offending lights; (2) the arenas of emotional disturbances: such as post trauma stress disorder, anxiety, and/or panic attacks, phobias, addictions, eating disorders; and (3) the realm of concentration/attention span disturbances: such as attention deficit disorder and performance of precision/exacting tasks, seizures, headache syndromes, and gastro-intestinal tract disorders.

There are many other areas where it is desirable to isolate those hues that will provide optimal positive, strengthening stimuli to an individual's visual system and identify those shades which will have a negative weakening effect. These areas can be psychotherapeutic or non-therapeutic (that is, solely cosmetic or commercial in nature).

Prior art devices proposed in an attempt to identify colors which may prove optimal to an individual for one reason or another, include the imagescope described in U.S. Pat. No. 4,327,712, issued May 4, 1982 to Frenkel et al; and, an associated device to be used in combination with an imagescope as described in U.S. Pat. No. 5,064,410, issued Nov. 12, 1991 to Frenkel et al.

SUMMARY OF THE INVENTION

The invention pertains to a color reactivity detecting device for testing individuals in order to identify the specific hues of colors, that will have an effect on the individual either in a positive, strengthening, or a negative, weakening way. That is, the apparatus will determine with respect to each individual, the particular color hues which are optimal for that individual in terms of reducing stress or promoting peak performance in mental, academic, work or physical endeavors. Such shades, once identified, can be used advantageously by the individual in a variety of therapeutic and/or non-therapeutic ways.

The apparatus can also identify those particular hues of colors, that can adversely affect the individual in terms of inducing anxiety, or negatively altering the strength or mood of the individual. This drives the person into self-defeating and/or self-destructive behaviors in an attempt to avoid such negative, weakening shades.

The apparatus also detects innately neutral colors with respect to each individual. It detects and analyzes the innate color reactivity quotient of the individual independent of subjective responses, verbal or otherwise, from this individual.

The color reactivity detecting device includes a patient interface apparatus where the patient is isolated and interfaced with color stimuli while fitted with biofeedback sensors in order to monitor biological system responses in response to the changing hue scheme. A microprocessor is provided to conduct a color stimuli presentation to the patient and simultaneously process the biofeedback responses generated by the patient; a monitor station is provided to view the coordination of the biofeedback responses of the patient with the color stimuli. The monitor station can include sub-stations comprised of a printer and of a therapist station with a cathode ray tube for viewing the biofeedback responses as a function of color stimuli.

IN THE DRAWINGS

DESCRIPTION OF PREFERRED EMBODIMENTS

Figure 1:
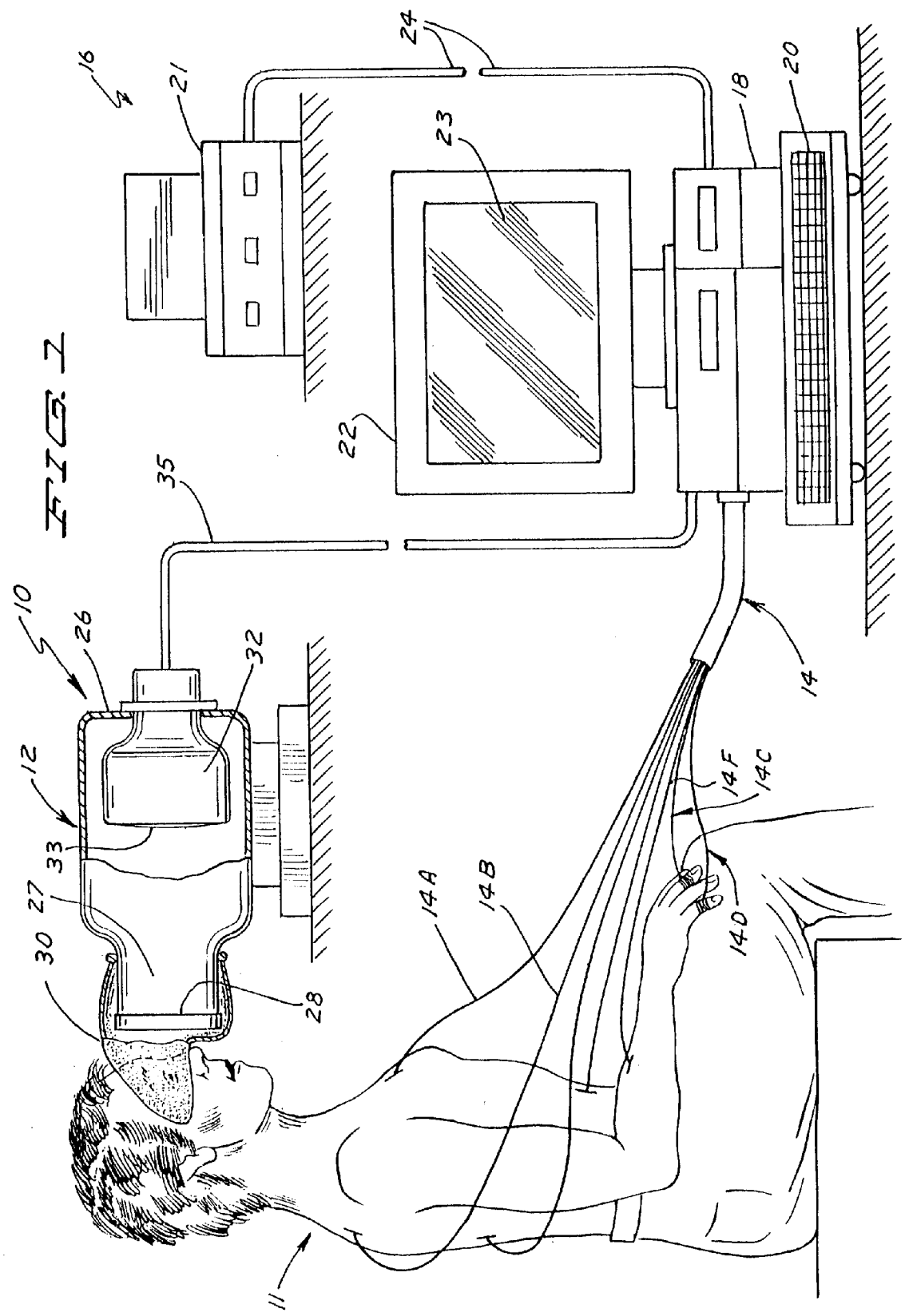
FIG. 1 is a side elevational view depicting a patient interacting with a color reactivity device according to the invention, partly in section for purposes of illustration.

Referring to the drawings, there is shown in FIG. 1 a color reactivity device according to the invention, the composite of which is indicated generally at 10. A patient, indicated at 11, is situated in working relationship to the detecting apparatus 10. The patient 11 is provided with an isolated view of a changing color scheme, changing through various hues of each color so that the patient, in isolation, views the color scheme while connected to a biofeedback sensor assembly. The biofeedback sensor assembly monitors certain body functions such as EMG, EEG, skin conductance, skin temperature, heart rate, blood volume pulse, blood pressure and respiration. It can monitor all of these functions or selected of these functions in combination. It can monitor absolute values or deviation from a norm or base line for the patient. These various body parameters will change according to the psychological response of each patient to the changing hues, as indicated by the signals generated by biofeedback sensors. These involuntary, subjective bodily function responses are recorded in time coordination with the changing color scheme in order to correlate them for future reference and use by or on behalf of the patient 11.

As shown in FIG. 1, the color reactivity device includes a patient interface apparatus 12 where the patient perceives a presentation of hues of colors. The color reactivity device also includes an assembly of biofeedback sensors 14 strategically connected to body parts to objectively monitor patient response to the color presentation. The color reactivity device also includes a microprocessor station 16. This includes one or more microprocessors 18 that may or may not be housed in a common cabinet, and having input-output devices typically including a keyboard 20, a CRT monitor 22, and a printer 21. The peripheral devices are connected to the microprocessor(s) by suitable multi-pin connector cables 24.

The patient interface apparatus 12 includes a cabinet or housing 26 having a necked-in sidewall portion forming a neck 27 defining a patient view port 28. The patient 11 faces the view port 28 to view the interior of the cabinet. One end of a shroud 30 connects to the neck 27. The shroud 30 can cover facial portions of patient 11 for purposes of further isolating the viewing area of the patient 11 and concentrating the attention of the patient on the display screen.

A video tube CRT or computer monitor 32 is mounted at the end wall of housing 26 opposite the neck 27 and positioned such that the patient 11, when properly situated at the viewing port 28, can clearly see the screen 33 of the CRT and little, if anything, more, due to the isolation provided by the housing 26 and shroud 30. This encourages the patient's undivided attention to the display on the screen. A data cable 35 transmits data to the CRT from a microprocessor. The data is in the form of a color hue display for viewing by the patient.

The processing station 16 contains one or more microprocessors as may be needed in order to generate a color scheme scenario performed for the patient at the video monitor of the patient apparatus; receive the biofeedback responses from the biofeedback sensors, and display and coordinate these with the color display for direction to the output devices. The color scheme or display can be generated in a format of colors changing with respect to color and hue as a function of time presented on the video monitor. Such a display can be constructed through conventional means using available programs, such as the paint brush program found in the Windows operating system sold by Microsoft Corporation, or the Painter program, version 2, sold by Fractal Design Company.

The processing station 16 processes the biofeedback sensor responses, coordinating them with the color display and feeds the information to output means that can include a printer 18 and a computer monitor station 20. The printer 18 records the various biofeedback responses of the patient in coordination with the color display. A therapist at the monitor station 20 can view the same information on a video monitor.

Biofeedback sensors 14A–14H are strategically placed on the body of patient 11 in known fashion and usually in accordance with the instructions of the vendor or manufacturer of the sensors. Each sensor is specifically selected to measure a particular body function response. Measurements are made of body functions susceptible to objective, involuntary response under the influence of color stimuli. Examples of body function responses that can be measured include EMG, EEG, skin conductance, skin temperature, heart rate, blood volume pulse, blood pressure and respiration. Preferably, a plurality of there parameters are measured simultaneously. An example of a biofeedback sensor assembly is that sold by Thought Technologies Ltd. under the trademark ProComp. Such a system uses active biofeedback sensors using micro miniature preamplifiers at muscle sites. This system is suitable for use with a 386 or 486 driven microprocessor. Sensor outputs can be processed independently. The results can be noted with respect to absolute values or with respect to a deviation from a patient base line, or in such other output format as may be desirable.

Figure 2:
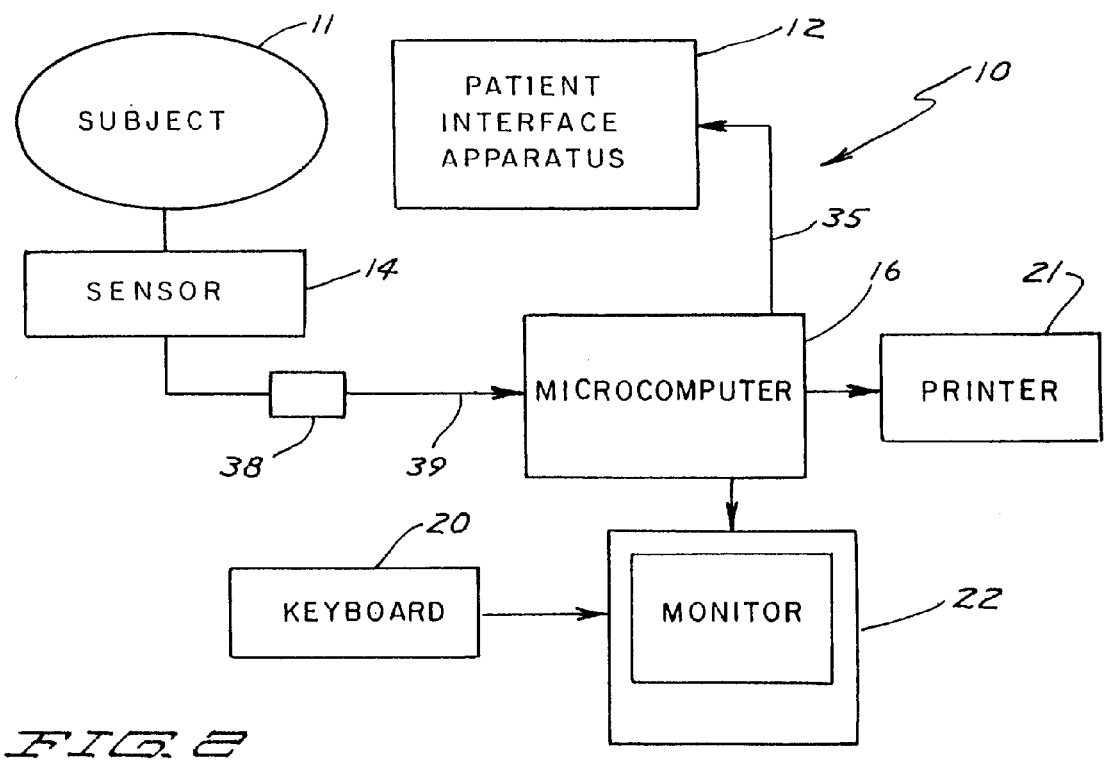
FIG. 2 is a schematic diagram of the color reactivity device of FIG. 1.

FIG. 2 presents a diagram that depicts the color reactivity device 10. The patient 11 is equipped with the sensors 14 of a biofeedback assembly and views a display provided at the patient interface apparatus 12. The display is provided from the microprocessor station 16 via data cable 35. As the patient views the display, the changing color display invokes involuntary mental or emotional responses from the patient according to the colors and hues displayed. These responses are directly reflected by changes in the biological functions monitored by the sensors. The responses are objective and the data is derived without effort on the part of the patient. The sensors 14 transmit encoded response signals to the microprocessor station 16, through a sensor interface module 38, as may be necessary according to the particular equipment in use. Module 38 can contain interface and conditioning electronics for the sensor, an analog to digital convertor, and micro computer interface (such as a serial S-232 interface). Microprocessor station 16 could include a remote microprocessor on site with the patient, or even integrated with the sensor assembly, in a situation, for example, where the patient is remote from a therapist.

The data from the biofeedback sensor assembly is processed and delivered to the output devices for viewing by the therapist. The data can optionally be stored in memory for later analysis. A keyboard 20 can be used to issue commands to the microprocessors, such as stop, start, delay, or to alter program variables.

Figure 3:
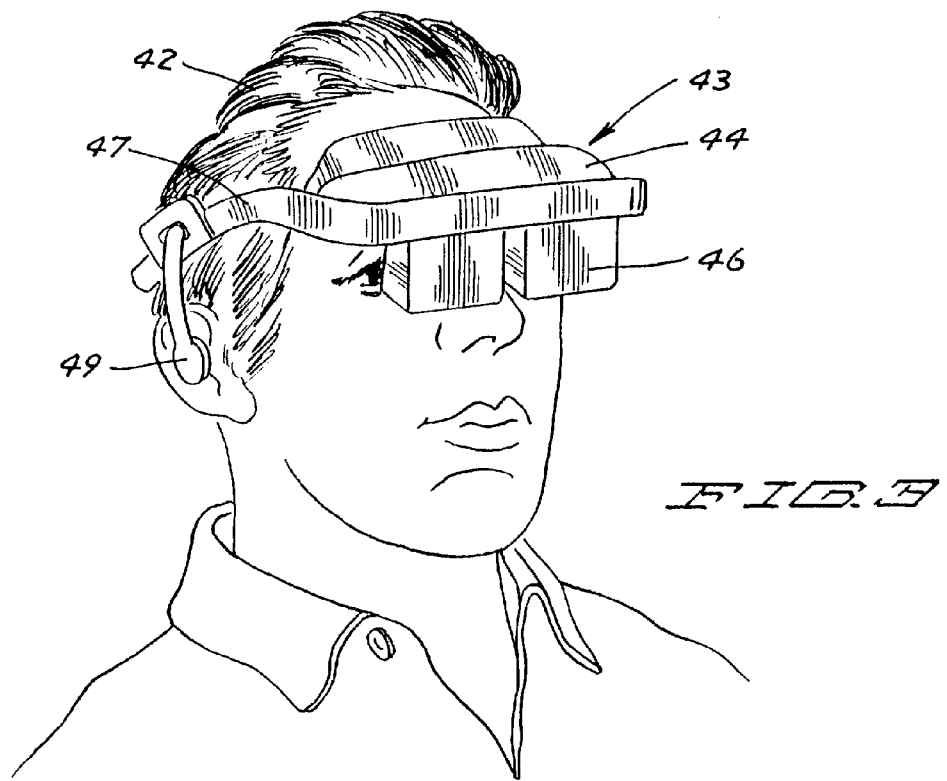
FIG. 3 illustrates a patient interacting with an alternative form of patient interface apparatus.

FIG. 3 illustrates the use of an alternative form of patient interface apparatus. Video viewing devices have recently been developed that are worn on the head of the user to provide an isolated, undistracted video display. A patient 42 is shown wearing such a video device 43 which includes a frame 44 supported on the head of patient 42 by eyeglass-type bows 47. The frame carries liquid crystal display type video viewing screen devices 46. The patient can also wear earphones 49 to provide appropriate background noise or simply block outside, distracting noise. Advances in miniaturization may permit other components of the color reactivity device to be incorporated into a small unit such as a head worn unit.

In terms of a method, there is provided an electronically generated display of changing color hues, viewed by a patient. A biofeedback sensor assembly fitted to the patient is used to measure selected body functions susceptible of involuntary response upon viewing by the patient of influential color stimulus. These can include EMG, EEG, skin conductance, skin temperature, heart rate, blood volume pulse, blood pressure and respiration. Output signals from the biofeedback sensors are fed to a microprocessor for processing and coordination with the color display to determine color influence upon the individual patient. In particular, optimal color hues are determined, and detrimental color hues can be isolated as well.

Once derived, the patient data is extremely useful to and on behalf of the patient, by means that have been previously described, and in numerous other applications: (1) isolation of positive and negative color hues can be used in the treatment of addictions. Saturation of a person's internal environment with positive color hues (thus, eliminating the negative ones), can help defuse the internal conflict of the individual that leads to substance abuse or other detrimental behavior in order to blunt the side-effects of the bombardment of their most negative hue; (2) it can ameliorate S.A.D. (seasonal affective disorder) which affects many persons during the sunlight and day-shortened winter months; (3) the symptoms of P.T.S.D. (post trauma stress disorder) and other stress-related syndromes can be managed and even eliminated; (4) anxiety and/or panic attacks, as well as headache syndromes, can be aborted; (5) seizure disorders, including epilepsy, can be controlled and possibly resolved; (6) phobias and eating disorders can be overcome; and (7) hypertension, computer fatigue, attention deficit disorder, and gastrointestinal disorders (ulcers, etc.) have also responded well to this process.

FIGS. 4 through 7 depict an alternative embodiment of a color reactivity device according to the invention whereby the color display provided to the subject is of a true or pure color as opposed to a color display of the type generated by a cathode ray tube. The CRT produces perceived colors that are the product of a dot matrix combination of red, green and blue. The color perceived is not true color.

The human eye detects different colors of light over a wave length range of 350 to 750 nanometers. If the entire spectrum is viewed its color would be white. When only a portion of the spectrum is viewed, then a distinct, pure color is perceived, as opposed to a perceived color that is the resultant of a dot matrix mixture of the colors red, green and blue. In real life, an individual primarily receives true color. Accordingly it is preferable to determine the color reactivity of a person using displays of true colors.

Figure 4:
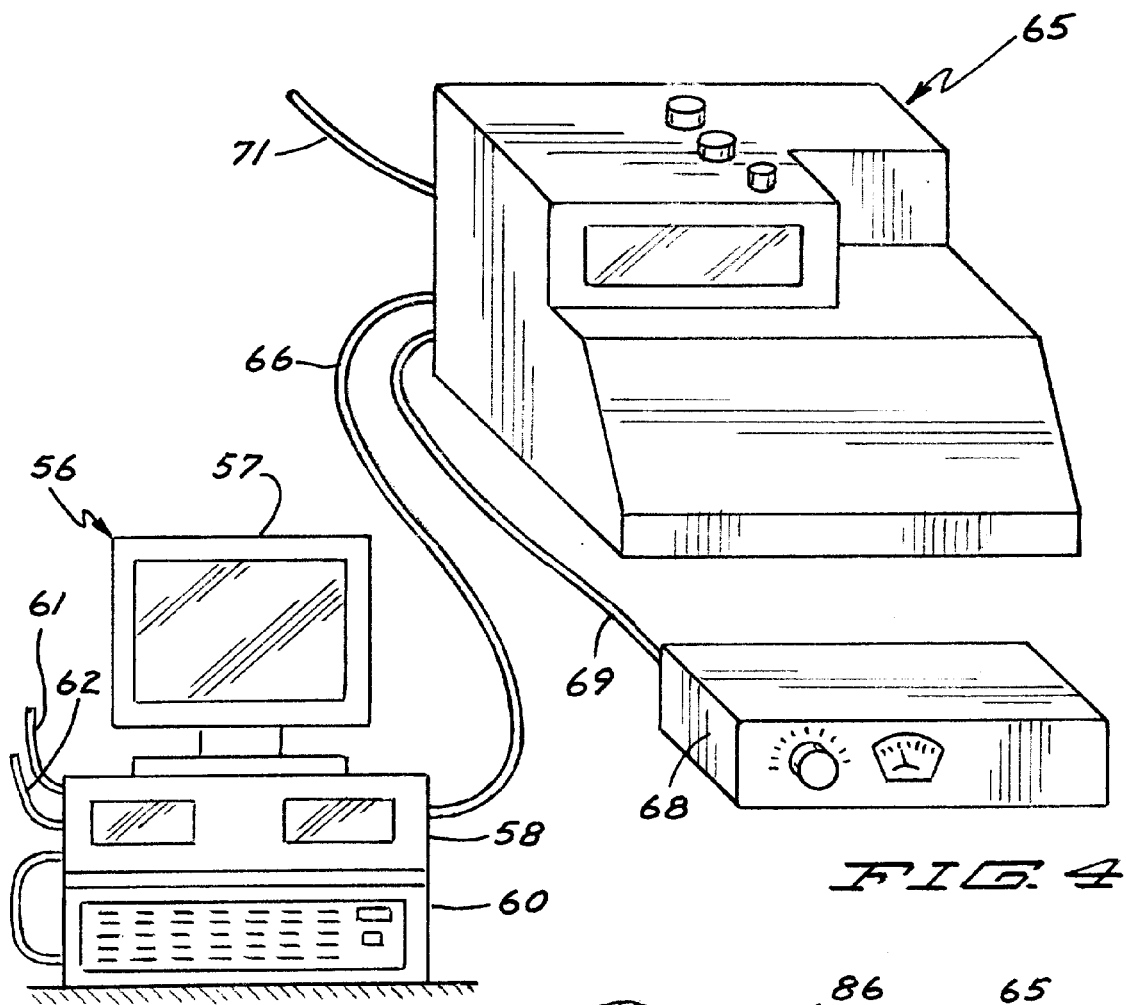
FIG. 4 depicts components of a color reactivity apparatus according to an alternative embodiment of the invention.
Figure 7:
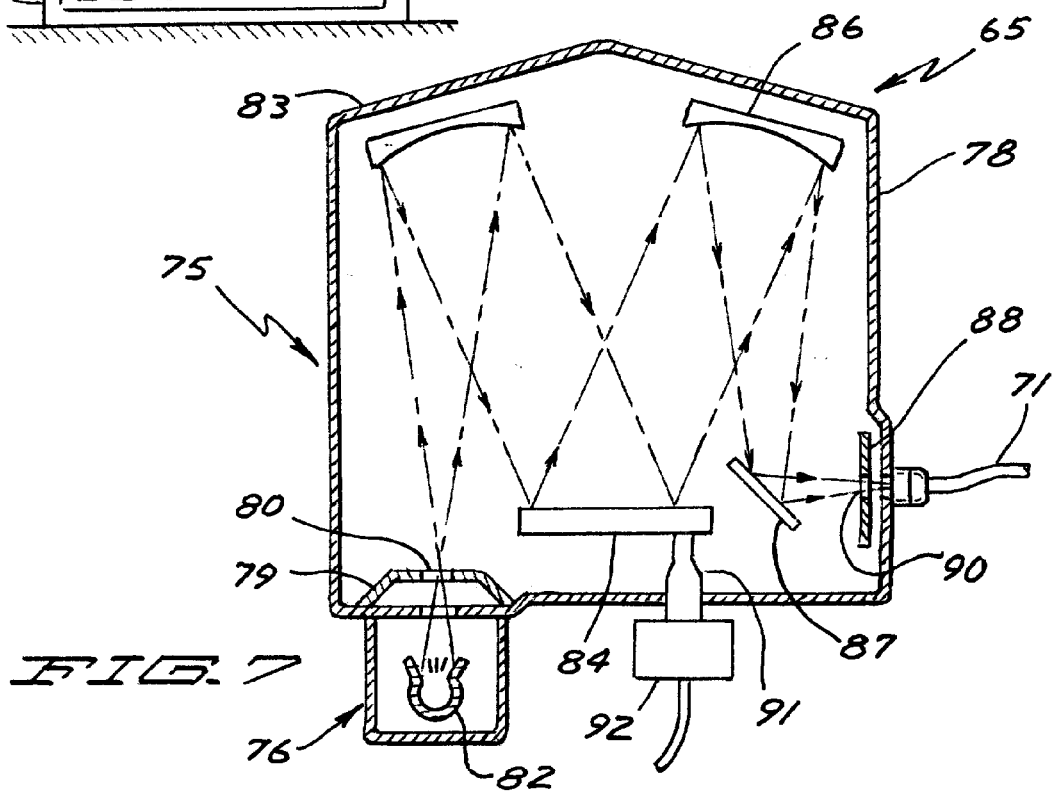
FIG. 7 is a schematic view of the monochromatic light source assembly of the embodiment of FIG. 4 showing a monochromator and a light source.

FIG. 4 depicts components of this alternative embodiment of the invention, including a computer 56 having a monitor 57, a central processing unit 58 and a keyboard 60. The color reactivity device includes a monochromatic light source device 65 connected to the CPU by a control cable 66.

A sensor input cable 61 connects the CPU to the biofeedback assembly as previously described, and an output cable 62 connects to an output device such as a printer.

Monochromatic light source device 65 provides a color display comprised of a single color or hue consisting of radiation of a single wavelength or a very small wavelength range. Monochromatic light source device includes a monochromator and a light source, both schematically depicted in FIG. 7, and a power supply 68 connected by a power cable 69. The monochromatic color emitted by the monochromatic light source 65 is transmitted by an optic fiber cable 71 to a head-worn patient interface device 72 shown in FIGS. 5 and 6.

The monochromator 65 is manufactured by Optical Technology Devices, Inc. of Elmsford, N.Y. It includes a light proof housing 78 having an entrance port covered by an entrance plate 79 with an entrance slit 80. Light source 76 is focused upon the entrance slit 80.

Light source 76 includes a lamp 82 that radiates a continuous visual spectrum of light. For example, this can be a 150 watt xenon arc lamp that radiates electromagnetic energy over a wavelength range exceeding 350–750 nm.

Radiation from the lamp 82 is focused upon the slit 80. A spherical collimating mirror 83 located in housing 78 is positioned in alignment with the plane of entrance slit 80 to collect all radiation passing through the slit. Collimating mirror 83 directs the collected radiation to an optical diffraction grating 84. The diffraction grating 84 transmits reflected wavelength radiation to a focusing mirror 86. Focusing mirror 86 focuses the received radiation and directs it to a plane mirror 87. An exit plate 88 has an exit slit 90 facing an exit port in housing 78. Plane mirror 87 focuses the monochromatic energy upon the plate 88 where it passed through the exit slit 90. The fiber optic cable 71 is connected to the exit port of housing 78.

The setting of diffraction grating 84 is regulated by dial control 91. Dial control 91 is operated by a stepper motor 92. Stepper motor 92 is connected to the CPU 58. The diffraction grating separates the light energy into its component wavelength parts. It performs this function by diffraction which bends different wavelengths different amounts separating the wavelengths into distinctly identifiable bands of color.

Exit plates 88 are interchangeable to provide various widths of exits slits 90. The width of the exit slit 90 in part controls the spectral wavelength bandwidth of the light that leaves the exit port of the monochromator. Slit widths from 2.5 to 20 nm can be used. The color of light is changed by rotating the optical grating so that different wavelengths of light pass through the exit slit of the monochromator.

Figure 5:
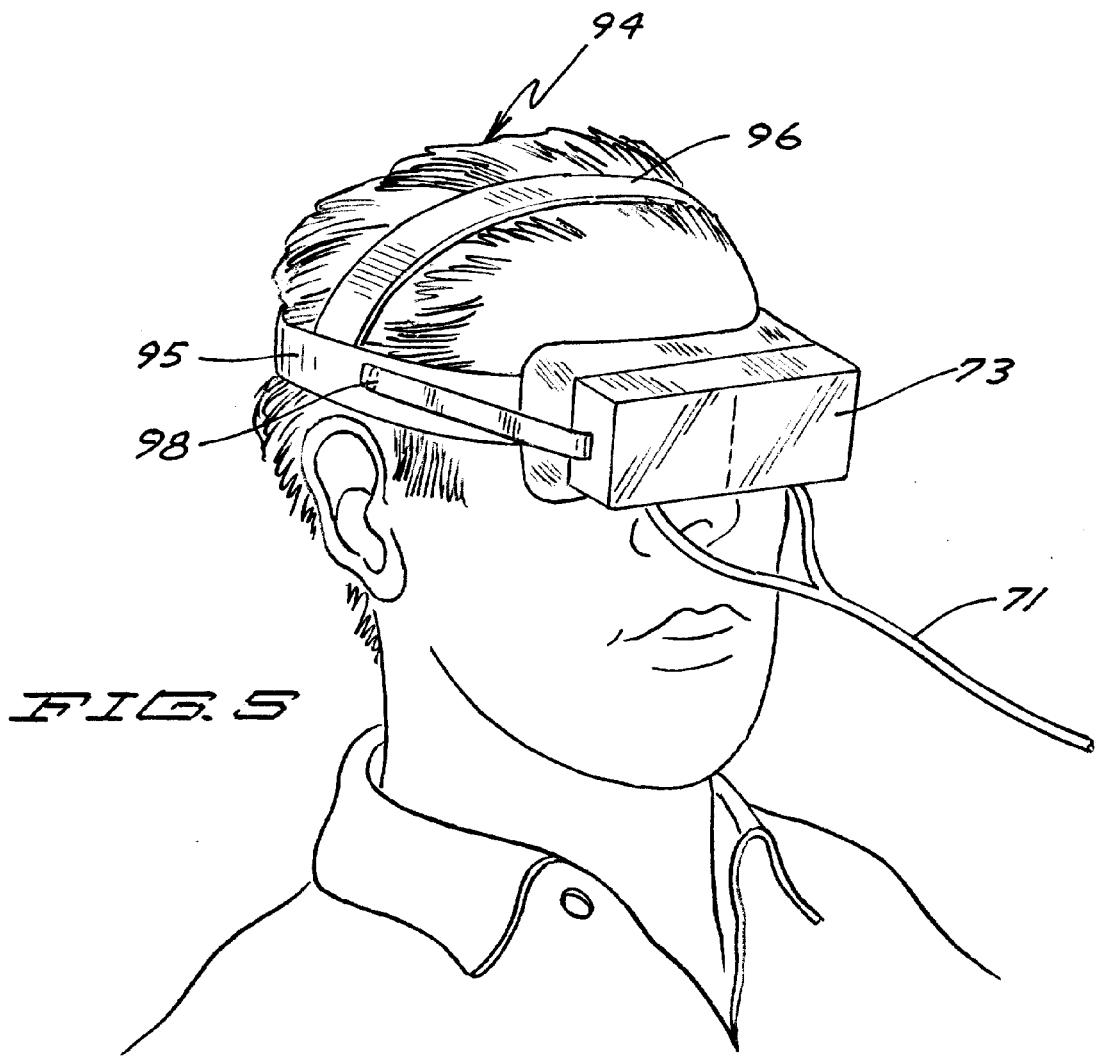
FIG. 5 depicts a patient wearing a patient interface apparatus of the embodiment of the invention shown in FIG. 4.
Figure 6:
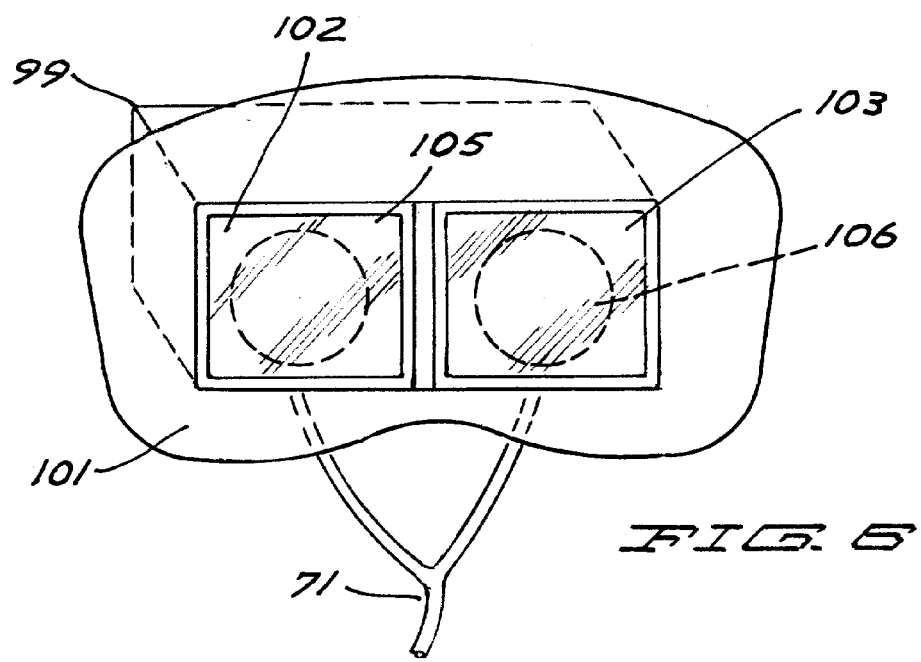
FIG. 6 is a patient view as seen when wearing the patient interface apparatus of FIG. 5.

FIGS. 5 and 6 illustrate a patient interface apparatus for use with the components of the invention shown in FIG. 4. A patient 94 wears the apparatus 73. The apparatus includes head gear or a head mount frame having a horizontal band 95 that circumferentially fits around the upper portion of the head of the subject. A semi-circular vertical band 96 connects to the horizontal band 95 and is disposed over the top of the head. Arms 98 are pivotally attached to the frame at one end. The opposite ends of arms 98 carry a sight module 99 that fits over the eyes of the subject 94. A soft rubber apron 101 is attached to the perimeter of the sight module in confronting relationship to the face of subject 94. Apron 101 is for purposes of comfort and provides a visual seal around the perimeter of the sight module.

Sight module 101 is divided into left and right optical mixing and viewing chambers 102, 103. Each chamber is connected to the fiber optic cable 71 to receive the identical color display from it. FIG. 6 depicts the display seen by the patient. Each chamber contains a diffuser screen or plate. The color beam transmitted through the optic fiber cable projects upon the diffuser screen on the side thereof opposite the eye of the patient. The diffuser screen diffuses the light beam to project a circular image indicated at 106 in FIG. 6. This is the display of pure color experienced by the patient, isolated from any other visual stimuli by the apron 101.

CPU 58 is provided with a computer program that controls stepper motor 92 to sequence through a display of colors or hues. The program can provide a display of each hue for a timed interval. Alternatively, manual advancement through the sequence of hues can be provided controlled by either the patient or the technician. Simultaneously, the involuntary reactions of the patient are monitored and recorded. The data can be stored on the hard disc of the CPU or converted to hard copy with the printer. The color display perceived by the patient is of pure or true colors. This enhances the accuracy and usefulness of the data.

While certain preferred embodiments of the invention have been shown and described, it is apparent that deviations can be promulgated without departing from the scope and spirit of the invention.

I claim:

1. A color reactivity device, to derive with respect to an individual, particularly influential color hues, comprising:

a patient interface means including a display means for presentation of a successive display of different hues of color during a time interval;

means for isolation of the viewing field of the patient in order to concentrate the attention of the patient on the display means;

biofeedback means connectable to a patient, to measure selected objective body function responses of the patient which are susceptible to involuntary response to visually perceived color stimuli, and convert the responses to electric data signals;

means for providing a color display at the patient interface means display means including a color display program having means for successively presenting a plurality of individual color hues for viewing by the patient;

said means for providing a color display at the patient interface means including a monochromatic light source;

an optic fiber cable connecting the display means to the monochromatic light source;

said display means including a head-worn device that includes a frame to fit on the head of a patient;

a sight module carried by the frame;

said sight module having right and left optical chambers viewable by the patent when wearing the frame, said fiber optic cable connected to the optical chambers, and diffuser means in the optic chambers to provide display of pure color to the patient;

computer processor means connected to the biofeedback means for processing body function response data of the patient; and output means connected to the computer processor means to generate an output display of processed data showing body function response in coordination with each color hue presented by the color display program.

2. The color reactivity device of claim 1 wherein:

said biofeedback means includes a biofeedback assembly having a plurality of biofeedback sensors connectable to the body of the patient.

3. The color reactivity device of claim 2 wherein:

said biofeedback assembly includes a plurality of biofeedback sensors each specifically selected to measure a bodily function chosen from the following list: EMG, EEG, skin conductance, skin temperature, heart rate, blood volume pulse, blood pressure, and respiration.

4. The color reactivity device of claim 1 wherein:

said computer processor means includes a microprocessor.

5. The color reactivity device of claim 4 wherein:

said output means includes a computer monitor.

6. The color reactivity device of claim 5 wherein:

said output means includes a printer.

7. The color reactivity device of claim 6 wherein:

said output means includes a computer monitor and a printer.

8. The color reactivity device of claim 7 wherein:

said biofeedback means includes a biofeedback assembly having a plurality of biofeedback sensors connectable to the body of the patient.

9. The color reactivity device of claim 8 wherein:

said biofeedback assembly includes a plurality of biofeedback sensors each specifically selected for the purpose of measuring a bodily function chosen from the following list: EMG, EEG, skin conductance, skin temperature, heart rate, blood volume pulse, blood pressure, and respiration.

10. The color reactivity device of claim 1 wherein:

said monochromatic light source includes a monochromator in conjunction with a lamp that radiates a continuous visual spectrum of light.

11. A method of determining, with respect to an individual, particularly influential color hues, comprising:

providing a display means and isolating the field of view of the individual so that the individual sees substantially only a display on the display means;

providing a monochromatic light source connected to the display means for viewing by the individual a display consisting of a succession of changing color hues generated by the monochromatic light source during a time interval;

using biofeedback sensors for electronically measuring objective body function responses of the individual to each individual color hue, while the patient is viewing the color display, chosen from the following list: EMG, EEG, skin conductance, skin temperature, heart rate, blood volume pulse, blood pressure, and respiration;

using a computer processor to process measurement data provided by the biofeedback equipment and coordinate it with the color display; and displaying the processed data.

* * * * *